United States Patent
Rinnert et al.

(10) Patent No.: US 8,530,722 B2
(45) Date of Patent: Sep. 10, 2013

(54) DISPOSABLE DIAPER HAVING NONWOVEN TOPSHEET WITH PARTICULAR COMBINATION OF BASIS WEIGHT AND BONDING CONFIGURATION

(75) Inventors: Thorsten Rinnert, Fernwald (DE); Manuela Schneider, Bensheim (DE); Nicole Anja Reichardt, Sulzbach am Taunus (DE); Bettina Kruse, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 61 days.

(21) Appl. No.: 13/167,789

(22) Filed: Jun. 24, 2011

(65) Prior Publication Data
US 2011/0319846 A1    Dec. 29, 2011

(30) Foreign Application Priority Data

Jun. 25, 2010 (EP) .................................... 10167333
Feb. 22, 2011 (EP) .................................... 11155400

(51) Int. Cl.
*A61F 13/511*    (2006.01)
(52) U.S. Cl.
USPC .......................................... 604/366; 604/370
(58) Field of Classification Search
USPC .................................................. 604/366, 370
See application file for complete search history.

(56) References Cited

U.S. PATENT DOCUMENTS

| | | | |
|---|---|---|---|
| 3,860,003 A | 1/1975 | Buell | |
| 4,695,278 A | 9/1987 | Lawson | |
| 4,795,454 A | 1/1989 | Dragoo | |
| 4,808,478 A | 2/1989 | Dana et al. | |
| 4,846,813 A * | 7/1989 | Raley | 604/385.08 |
| 5,171,239 A * | 12/1992 | Igaue et al. | 604/385.29 |
| 5,196,000 A * | 3/1993 | Clear et al. | 604/385.29 |
| 5,383,988 A * | 1/1995 | Herrmann et al. | 156/64 |
| 5,454,803 A * | 10/1995 | Sageser et al. | 604/385.28 |
| 5,536,555 A * | 7/1996 | Zelazoski et al. | 428/138 |
| 5,591,149 A * | 1/1997 | Cree et al. | 604/378 |
| 5,656,232 A * | 8/1997 | Takai et al. | 264/518 |
| 5,830,555 A * | 11/1998 | Srinivasan et al. | 428/137 |
| 5,954,705 A * | 9/1999 | Sawaki et al. | 604/385.101 |
| 6,013,349 A * | 1/2000 | Takeuchi et al. | 428/152 |
| 6,103,953 A * | 8/2000 | Cree et al. | 604/365 |
| 6,231,555 B1 * | 5/2001 | Lynard et al. | 604/385.01 |
| 6,319,239 B1 * | 11/2001 | Daniels et al. | 604/385.01 |
| 6,548,731 B2 * | 4/2003 | Mizutani et al. | 604/365 |
| 6,699,228 B1 * | 3/2004 | Chmielewski et al. | 604/385.28 |
| 6,747,186 B2 * | 6/2004 | Shimizu | 604/364 |
| 6,888,046 B2 * | 5/2005 | Toyoshima et al. | 604/380 |
| 7,105,715 B2 * | 9/2006 | Carlucci et al. | 604/361 |
| 7,402,157 B2 * | 7/2008 | Christon et al. | 604/385.01 |

(Continued)

OTHER PUBLICATIONS

International Search Report (PCT) mailed Oct. 13, 2011.

(Continued)

*Primary Examiner* — Susan Su
(74) *Attorney, Agent, or Firm* — William E. Gallagher; Richard L. Alexander

(57) ABSTRACT

A disposable diaper is disclosed. The diaper includes a colored topsheet. The topsheet has a basis weight of from 12 to 18 gsm and comprises a plurality of bonded points. Each of the bonded points has a surface area of from 2 mm² to 5 mm² and the cumulated surface area of the plurality of bonded points is from 10 to 25% of the total surface area of the topsheet.

15 Claims, 1 Drawing Sheet

(56) References Cited

U.S. PATENT DOCUMENTS

| | | | |
|---|---|---|---|
| 7,534,928 B2* | 5/2009 | Sakamoto et al. | 604/378 |
| 7,569,264 B2* | 8/2009 | Toyoshima et al. | 428/156 |
| 7,674,949 B2* | 3/2010 | Wahlstrom et al. | 604/380 |
| 7,824,385 B2 | 11/2010 | Ecker et al. | |
| 2003/0078553 A1 | 4/2003 | Wada et al. | |
| 2003/0187415 A1 | 10/2003 | Kudo et al. | |
| 2004/0167486 A1* | 8/2004 | Busam et al. | 604/367 |
| 2004/0170813 A1 | 9/2004 | Digiacomantonio et al. | |

OTHER PUBLICATIONS

International Search Report (EP) mailed Oct. 13, 2011.

* cited by examiner

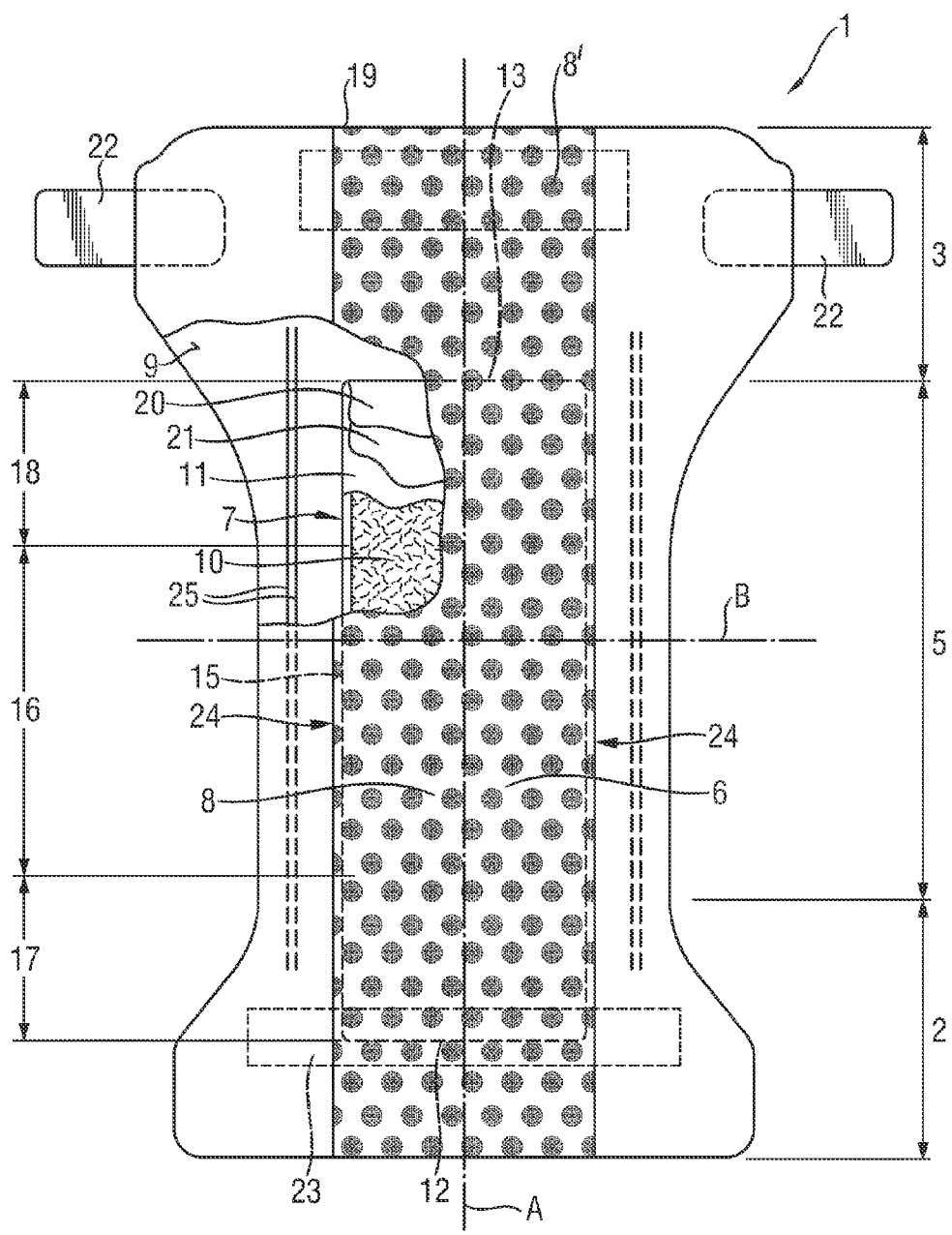

DISPOSABLE DIAPER HAVING NONWOVEN TOPSHEET WITH PARTICULAR COMBINATION OF BASIS WEIGHT AND BONDING CONFIGURATION

FIELD OF THE INVENTION

The invention refers to disposable diapers which show good performances, are soft to the touch in these regions contacting the skin of the wearer and are appealing to consumers.

BACKGROUND OF THE INVENTION

Disposable absorbent articles for receiving and retaining bodily discharges such as urine or feces are well known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

Since their introduction into the market place, disposable diapers have continued to improve regarding comfort, fit and functionalities. While absorption capacity is quite important for diapers, consumers also appreciate products having a soft feel to the touch, especially in these regions of the diaper which directly contact the skin of the wearer, such as the diaper's topsheet. Many attempts have been made to increase the softness of the topsheet, such as by selecting a particular fiber type or by reducing fibers bonding within the material e.g. a nonwoven material, used for the manufacturing of the topsheet. Typically, fibers' bonding imparts strength to the material. Strength is needed to provide resistance to tearing during use of the diaper and also during the manufacturing process. Unfortunately, when steps are undertaken to increase the softness of the topsheet, such as decreasing the bonding area to increase softness, strength may be adversely affected.

In addition to this technical challenge, i.e. increasing softness without compromising strength, it was observed that consumers tend to prefer diapers having a topsheet with a bonding pattern which is highly distinguishable wife naked eyes. Such a highly visible bonding pattern increases the attractiveness of the product and also non-negligibly increases the perception of softness that the consumers may have of the product. Unfortunately, at today's used basis weight, the bonding pattern on the topsheet is barely noticeable by consumers. Whilst increasing the basis weight of the material forming the topsheet may desirably enhance the visual distinction of the bonding pattern, it was found that other physical properties of the topsheet were adversely affected. For instance, in an undesirable way, the liquid retention properties of the topsheet were increased. As well it was found that increasing the bonding area to make it more visible was not desirable since it decreases the softness of the topsheet, contributes to provide a non-desirable plastic feel to the topsheet and increases the risk that the liquid runs off the topsheet. Hence, the negative effects obtained when seeking to increase the visibility of the bonding pattern on the liquid handling properties of the topsheet add even more complexity to the already known technical challenges to create diapers which are soft to the skin, have desired fluid management properties and which are highly attractive to the consumer.

Hence, there is a need for disposable diapers which are soft to the skin, have desired fluid management properties, such as desired fluid permeability and low rewet and which are highly attractive to the consumer.

SUMMARY OF THE INVENTION

The invention relates to a disposable diaper including a colored topsheet. The topsheet has a basis weight of from 12 gsm to 18 gsm and comprises a plurality of bonded points. Each of the bonded points has a surface area of from 2 mm$^2$ to 5 mm$^2$ and the cumulated surface area of the plurality of bonded points is from 10% to 25% of the total surface area of the topsheet.

BRIEF DESCRIPTION OF THE DRAWINGS

FIG. 1 is a plan view of a diaper.

DETAILED DESCRIPTION OF THE INVENTION

As used herein "diapers" refers to devices which are intended to be placed against the skin of a wearer to absorb and contain the various exudates discharged from the body. Diapers are generally worn by infants and incontinent persons about the lower torso so as to encircle the waist and legs of the wearer. Examples of diapers include infant or adult diapers and pant-like diapers such as training pants.

"Training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

As used herein "disposable" refers to devices which are generally not intended to be laundered or otherwise restored or reused (i.e., they are intended to be discarded after a single use and, may be recycled, composted or otherwise disposed of in art environmentally compatible manner).

"Nonwoven material" as used herein refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which may comprise spunlaying, meltblowing, carding, airlaying, wetlaying, coform and combinations thereof. The fibers may be of natural or man-made origin and may be staple fibers or continuous filaments or be formed in situ.

"Particulate absorbent polymer material" as used herein refers to substantially water-insoluble polymer particles that can absorb at least 5 times their weight of a 0.9% saline solution in de-ionized water as measured using the Centrifuge Retention Capacity test (Edana 441.2-01).

By "bonded points" as used herein, it is meant discrete areas of the topsheet wherein the fibers are melted and fused, i.e. heated to a temperature above their melting point. The bonded points can be provided by heat bonding or by a combination of pressure and heat bonding (the fibers are heated above their melting point).

The term "basis weight" as used herein refers to the mass of dry fibrous material per unit area, i.e. the mass of dry sheet per unit area, e.g. gram per square meter (gsm).

The Topsheet

The inventors found that a diaper including a colored topsheet, said topsheet having a basis weight of from 12 gsm to 18 gsm, or from 13 gsm to 16 gsm, or of 15 gsm, and a plurality of bonded points, wherein each of said points has a surface area of from 2 mm$^2$ to 5 mm$^2$, or from 2.5 mm$^2$ to 4.5 mm$^2$, or from 3 mm$^2$ to 4 mm$^2$, and wherein the cumulated surface area of the plurality of bonded points is from 10% to 25%, or from 14% to 22% or from 16% to 21%, of the total surface area of the topsheet solves the above mentioned problems.

Said topsheet of low basis weight, i.e. from 12 gsm to 18 gsm, or from 13 gsm to 16 gsm, or of 15 gsm, exhibits excellent fluid handling properties. Indeed, the inventors found that such a topsheet has the capacity to acquire liquid in a desirable way, i.e. the fluid, such as urine, readily penetrates through the thickness of the topsheet. Furthermore, the topsheet does not retain much fluids and thus minimizes the risk of rewet that may be observed when fluids are retained within the topsheet. Minimizing the rewet contributes to maintain die skin of the diaper's wearer in a dry state and thus to increase the comfort of the wearer.

The plurality of bonded points forms a pattern on the surface of die topsheet. The selected pattern, i.e. the plurality of bonded points having a surface area of from 2 mm$^2$ to 5 mm$^2$ or from 2.5 mm$^2$ to 4.5 mm$^2$, or from 3 mm$^2$ to 4 mm$^2$ and a cumulated surface area of from 10% to 25%, or from 14% to 22% or from 16% to 21% of the total surface area of the topsheet, confers an increased softness to the topsheet whilst not compromising its strength. Indeed, reducing the number of bonded points while increasing the surface area of each of die bonded point increases the unbonded area of the topsheet, i.e. more loose fibers are present on the surface of the topsheet, and thus increases its softness. Additionally, the combination of the selected pattern with a colored material of low basis weight enhances the visibility of the pattern on the surface of the topsheet. Indeed, it was found that the coloration of the topsheet enhances the glossy aspect of the bonded areas and thus contributes to enhance the visual distinction of the pattern on the topsheet. Overall, this increases the attractiveness of the product among consumers and overcomes the technical challenge of increasing the visibility of the pattern without compromising the fluid handling properties of the topsheet.

The topsheet may be a nonwoven material made of synthetic fibers alone or in combination with natural fibers. Examples of natural fibers may include cellulosic natural fibers, such as fibers from hardwood sources, softwood sources, starches or other non-wood plants. The synthetic fibers can be any material, such as, but not limited to, those selected from the group consisting of polyolefins (polypropylene and polypropylene copolymers, polyethylene and polyethylene copolymers), polyesters (e.g., polyethylene terephthalate), polyethers, polyamides, polyesteramides, polyvinylalcohols, polyhydroxyalkanoates, polysaccharides, and combinations thereof. Further, the synthetic fibers can be a single component (i.e. a single synthetic material or a mixture makes up the entire fiber), bi-component (i.e. the fiber is divided into regions, the regions including two or more different synthetic materials or mixtures thereof and may include co-extruded fibers and core and sheath fibers) and combinations thereof. Bi-component fibers can be used as a component fiber of the nonwoven material, and/or they may be present to act as a binder for the other fibers present in the nonwoven material. Any or all of the fibers may be treated before, during, or after manufacture to change any desired properties of the fibers. Preferably, the topsheet comprises at least 20% of synthetic fibers, or at least 30% of synthetic fibers or at least 50% of synthetic fibers. In some embodiments, the topsheet comprises 100% of synthetic fibers. Synthetic fibers are preferably thermoplastic fibers. Preferably, the topsheet is made of a nonwoven material made of a polyolefin, such as polyethylene, polypropylene or mixtures thereof. The topsheet may be a multilayer nonwoven web, i.e. a laminate. The laminate may comprise spunbond layer(s) (S), and/or meltblown layer(s) (M), and/or carded layer(s) (C). Suitable laminates include, but are not limited to, SS, SSS, SMS or SMMS. In some embodiments, the topsheet is a spunbond nonwoven material, such as a mono layer spunbond (S), or a dual layer spunbond (SS) or a nonwoven material comprising more than two layers, such as a spunbond nonwoven with three layers (SSS).

The topsheet comprises a plurality of bonded points. The cumulated surface area of the plurality of bonded points is from 10% to 25%, or from 14% to 22% or from 16%; to 21% of the total surface area of the topsheet.

The bonded points can take any shapes, such as circular, diamond, triangular, rectangular, square, oval or any other regular or irregular shapes. Each bonded point has a surface area of from 2 mm$^2$ to 5 mm$^2$, or from 2.5 mm$^2$ to 4.5 mm$^2$ or from 3 mm$^2$ to 4 mm$^2$. All die bonded points may have individually an equal surface area or they may have a variety of surface area.

It was found that when the cumulated surface area of the plurality of bonded points is of from 10% to 25%, or from 14% to 22% or from 16% to 21% of the total surface area of the topsheet, and when each point has a surface area of from 2 mm$^2$ to 5 mm$^2$, or from 2.5 mm$^2$ to 4.5 mm$^2$ or from 3 mm$^2$ to 4 mm$^2$, the resulting topsheet has a right balance in terms of softness and strength. Furthermore, it was found that the surface area of each of the bonded points, despite being relatively larger than commonly known bonding area, was suitably channeling the liquid through the topsheet, thus limiting the risk of liquid run off from the topsheet and the risk of leakage. Additionally, the large area of the bonded points was found to desirably communicate absorbency to consumers.

The plurality of bonded points may be distributed evenly over the topsheet. However, in some embodiment, the density of the plurality of bonded points may be higher at the longitudinal periphery of the topsheet compared to the center of topsheet. As used herein "longitudinal periphery of the topsheet" refers to one third of the topsheet area starting from the longitudinal edges of the topsheet and extending towards the longitudinal axis. Thus, there is a left side longitudinal periphery of the topsheet making up one third of the topsheet area, a right side longitudinal periphery of the topsheet making up another third of the topsheet area, and a center region making up the one third of the area in the center of the topsheet and crossing the longitudinal axis. Such embodiments are generally advantageous as the increased bonded area in the lateral areas can direct liquid which may otherwise run-off the topsheet, resulting in leakage, while the lower amount of bonded area in the central region ensures that the amount of topsheet available for liquid absorption is not unduly reduced. This is especially beneficial, as the fibers comprised by the bonded area are molten, which in turn can result in reduced absorbency in the bonded area.

The bonded area preferably does not extend into those layers of the disposable diaper which are positioned below the topsheet, such as the one or more layers of the acquisition system or the absorbent core. From a manufacturing point of view, these embodiments are advantageous, as the topsheet can be provided to the disposable diaper manufacturing line in pre-bonded and ready for assembly form. As such it can be joined with the other components of the disposable diaper (e.g. the absorbent core, backsheet) without need for further modification of me topsheet material. Thus, no additional process step is required in the disposable diaper manufacturing process.

In some embodiments, determining the actual dimensions of the bonded area on the topsheet material itself may be difficult as the change from non-bonded area to hooded area may be gradually. Therefore, for the present invention, die dimensions given herein for the bonded points are generally determined by the dimensions of the equipment used to provide the bonded pattern to die topsheet. Thus, while the dimensions can be approximated on the topsheet material, the pattern provided on the equipment has to be determined and are equated with the bonded area for the present invention. In embodiments, wherein the pattern used to provide the bonded area (such as the protrusions on an bonding roll or calendaring roll) do not have straight side-walls, the largest dimensions (i.e. the largest dimension of the width of the protrusions, not die height of the protrusions) on the equipment are considered to be the dimensions for the present invention.

The topsheet is colored. By "colored" as used herein, it is meant colored in a color other white, such as hut not limited to pink, yellow, purple, red, orange, blue, green, periwinkle and any declination thereof or mixture thereof. In some embodiments, the colored topsheet is colored in a pale or delicate variation of the color, i.e. the topsheet is tinted.

Colors can be measured according to an internationally recognized 3 D solid diagram of colors where all colors that are perceived by the human eye are converted into a numerical code. The system is based on three dimensions (x,y,z) and specifically L, a, b.

When a color is defined according to this system L represents lightness (0 black, 100 white), a and b independently each represent a two color axis, a representing the axis red/green (+a=red, −a=green), while b represents the axis yellow/blue (+b=yellow, −b=blue).

Any color is identified by a unique ΔE value which is mathematically expressed by the equation:

$$\Delta E = [(L_{ref}-L_{sample})^2+(a_{ref}-a_{sample})^2+(b_{ref}-b_{sample})^2)]_{1/2}$$

ΔE represents graphically the distance between the reference color and the no color point (i.e. centre of sphere $L_{ref}=50$, $a_{ref}=0$, $b_{ref}=0$) of die 3 D model.

Color can be measured using the colorimeter MINOLTA mode CR-300 instrument (available from the Minolta Company, Japan) which provides the coordinates L, a, b and from which the ΔE value can be determined.

The L Hunter scale values (L), utilized herein to define the darkness/lightness of the materials of the topsheet, are units of color measurement in the Hunter Color system, A complete technical description of the system can be found in an article by R. S. Hunter, 'photoelectric color difference Meter', Journal of the Optical Society of America, Vol. 48, pp. 985-95, 1958. Devices specially designed for the measurement of color on the Hunter scales are described in U.S. Pat. No. 3,003,388 to Hunter et al., issued Oct. 10, 1961. In general, Hunter Color "L" scale values are units of light reflectance measurement, and the higher die value is, the lighter the color is since a lighter colored material reflects more light. In particular, in the Hunter Color system the "L" scale contains 100 equal units of division, absolute black is at the bottom of the scale (L=0) and absolute white is at the tops of the scale (L=100). Thus in measuring Hunter Color values of the topsheet, the higher the "L" scale value, the lighter the material.

It is to be understood that the L Hunter values and color values ΔE considered herein are those measured on the materials of interest (e.g., topsheet), taken in layer or folded upon itself, so that upon additional layering of die same material or additional folding thereof, the L Hunter value and color value stay constant. Indeed the L Hunter value and ΔE are those of the material per se without any influence of the support onto which the material is disposed in the instrument for its measure. In other words, when measuring the L Hunter value of topsheet, several layers of this material are superposed or a layer thereof is folded upon itself several times before measuring its L Hunter value, the same material is measured again after additional layering or folding, this later operation is performed as needed until upon additional layering or folding the L Hunter value does not change any more. This value is the one to be considered herein.

In some embodiments, the colored topsheet has a L value from at least 60, such as from 60 to 95, or from 70 to 95, or from 80 to 90. A topsheet which is colored such that it fulfils the L Hunter value has a delicate or pale color.

In some embodiments, the colored topsheet has an "a" value from about −50.0 to about +50.0, or from about −30.0 to about +30.0, or from about −20.0 to about +20.0 or from about −10.0 to about +10.0. Furthermore, the colored topsheet has a "b" value from about −50.0 to about +50.0, or from about −35.0 to about +25.0, or from about −25.0 to about +5.0 or from about −20.0 to about +5.0.

The topsheet is colored all over its surface, typically uniformly colored all over its surface. Preferably, the topsheet is colored with a single color, typically uniformly colored all over its surface with a single color.

Coloring can be done by any methods available in the art. The topsheet may be colored after the manufacturing thereof or alternatively suitable pigments may be added to the material, e.g. polyolefin, out of which the fibers of the nonwoven material are made.

Suitable coloring agent may be generally termed as pigment which refers to an insoluble color matter used in finely dispersed forms. The coloring agents may be dyes, organic pigments or inorganic pigments. Exemplary organic pigments may include: C.I. Pigment Yellow 1, C.I. Pigment Yellow 3, C.I. Pigment Yellow 13, C.I. Pigment Red 5, C.I. Pigment Red 7, C.I. Pigment Red 12, C.I. Pigment Red 112, C.I. Pigment Red 122, C.I. Pigment Blue 1, C.I. Pigment Blue 2, C.I. Pigment Blue 16, C.I. Vat Blue 4, C.I. Vat Blue 6, or Carbon black. Exemplary inorganic pigments may include carbon black (e.g., Pigment Black 7), iron oxides, ferric oxide black (e.g., Pigment Black 11), chromium oxide, or ferric ammonium ferrocyanide. Exemplary dyes may include: Solvent Yellow 14, Dispersed Yellow 23, Metanil Yellow, Solvent Red 111, Dispersed Violet 1, Solvent Blue 56, Solvent Orange 3, Solvent Green 4, Acid Red 52, Bask Red 1, Solvent Orange 63, or Jet Black.

The inventors found that surprisingly a colored topsheet, i.e. a topsheet of any colors excluding white, enhances the visibility of the bonded pattern on the topsheet by conferring a glossy aspect to the bonded points. The ability of the surface to reflect light in a specular direction is different in the bonded areas vs. the non-bonded areas. As such, this enables to increase the visibility of the pattern without compromising the fluid handling properties of the topsheet.

Disposable Diaper Including the Topsheet of the Present Invention

The topsheet described herein may be incorporated into a disposable diaper 1 such as illustrated in FIG. 1. The disposable diaper 1 is shown in its flat out, un-contracted state (i.e. without elastic induced contraction) and some portions of the disposable diaper 1 are cut away to more clearly show the underlying structure of the disposable diaper. The portion of the disposable diaper 1 that contacts a wearer is facing the viewer in FIG. 1. The diaper 1 represented in FIG. 1 has a longitudinal axis A and a transverse axis B.

One end portion of the diaper is configured as a front waist region 2 (which is die front one third of the article, having one third of the length of the article). The opposite end portion is configured as a back waist region 3 (hack one third) of the diaper, having one third of the length of the article. An intermediate portion of the diaper is configured as a crotch region 5 (centre one third), which extends longitudinally between the front and back waist regions, also having one third of the length of the article. The crotch region 5 is that portion of the diaper which, when the diaper is worn, is generally positioned between the wearer's legs.

The disposable diaper 1 generally comprises a chassis 6 and an absorbent core 7 disposed in the chassis.

The chassis 6 of the diaper comprises a topsheet 8 with bonded points 8' such as described herein. The topsheet 8 is typically co-extensive with the chassis 6 of the diaper. The topsheet may include a skin care composition. The skin care composition may be colored. However, a colored topsheet as used herein does not refer to a topsheet colored by a skin care composition. If the skin care composition is colored, it may slightly modify the initial color of the colored topsheet. The chassis 6 typically also comprises a backsheet 9. The backsheet 9 may be vapor pervious but liquid impervious. The backsheet may prevent the fluids absorbed and contained in the absorbent structure from wetting materials that contact the absorbent article such as underpants, pants, pyjamas, undergarments, and shirts or jackets, thereby acting as a barrier to fluid transport. The backsheet can also allow the transfer of at least water vapor, or both water vapor and air through it. In some embodiments, the backsheet may comprise a laminate of a nonwoven and a thin plastic film such as a thermoplastic film having a thickness of 0.012 mm to 0.051 mm. Suitable backsheet films include those manufactured by Tredegar Industries Inc. of Terre Haute, Ind. and sold under the trade names X15306, X10962, and X10964.

The chassis 6 further includes an absorbent core 7 disposed between the topsheet 8 and the backsheet 9 of the diaper 1. The absorbent core 7 typically comprises absorbent material 10 such as cellulose fibers, modified cellulose fibers (cellulose fibers and modified cellulose fibers are typically referred to in die art as "air-felt"), particulate absorbent polymer material, absorbent foams, tissue, or mixtures thereof. Suitable particulate absorbent polymer material can be selected among polyacrylates and polyacrylate based materials, such as for example partially neutralized cross-linked polyacrylates or acid polyacrylate. Examples of polyacrylate based polymers very slightly cross-linked, or substantially not crosslinked at all are described in the PCT Patent Application WO 07/047,598.

In some embodiments, the absorbent core may comprise less than 5% by weight of cellulose, more typically less than 2% and most typically is cellulose free. The resulting absorbent structures have a reduced thickness in the dry state compared to conventional absorbent structure comprising cellulosic fibers. The reduced thickness helps to improve the fit and comfort of the absorbent article for the wearer.

In some embodiments, the absorbent core 7 may comprise one or more absorbent structure, each absorbent structure comprising a nonwoven substrate layer supporting particulate absorbent polymer material, said particulate absorbent polymer material being immobilized on the nonwoven substrate layer by a thermoplastic adhesive composition, which preferably forms a fibrous network over the particulate absorbent polymer material. Suitable thermoplastic adhesive compositions includes hot melt adhesives comprising at least a thermoplastic polymer in combination with a plasticizer and other thermoplastic diluents such as tackifying resins and additives such as antioxidants. Exemplary suitable hot melt adhesive materials are described in EP 1447067 A2. In some embodiments, the thermoplastic polymer has a molecular weight of more than 10,000 and a glass transition temperature usually below room temperature or comprised from $-6°$ C. to $16°$ C. In some embodiments, the concentration of the thermoplastic polymer in a hot melt is in the range of about 20 to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. The thermoplastic adhesive composition is generally present in the form of fibres forming a fibrous network over the particulate absorbent polymer material. The fibres may have an average thickness from about 1 μm to about 100 μm, or from about 25 μm to about 75 μm, and an average length from about 5 mm to about 50 cm. The thermoplastic adhesive composition may be applied at an amount of from 0.5 to 30 $g/m^2$, or from 1 to 15 $g/m^2$ or from 1 and 10 g/m or even from 1.5 and 5 $g/m^2$ per substrate layer. In some embodiments, the particulate absorbent polymer material is distributed in clusters of particles on the nonwoven substrate layer. In some embodiments, the absorbent structure comprises less than 5%, or less than 2% by weight of cellulose, or is cellulose free. The nonwoven substrate layer may enclose die absorbent polymer material and the thermoplastic composition or a separate nonwoven substrate layer may cover the absorbent polymer material and the thermoplastic composition. These nonwoven substrate layers are therefore often referred to as core wrap or core cover. The core wrap or core cover may consist of a first, upper nonwoven web 11 towards the body-facing surface of the absorbent article and of a second, lower nonwoven web (not shown in the FIGURE) towards the garment-facing surface of the absorbent article. The first and second nonwoven webs may be continuously or intermittently bonded to each other around their perimeters. The first and second substrate layers may be made of the same nonwoven webs or may be made of different nonwoven webs, i.e. the first, upper substrate layer may be fluid pervious whereas the second, lower substrate layer may be fluid impervious. In a multilayer absorbent core, one or more layers of a substrate (e.g. a nonwoven web) may additionally be placed within the absorbent core to at least partially separate and segment the particulate absorbent polymer material. The core wrap or core cover may be present in any types of absorbent core.

The periphery of the absorbent core 7 is defined by the outer absorbent core edges wherein the absorbent core front waist edge 12 and back waist edges 13 run between the longitudinal edges 15 generally parallel to the transverse axis A of the disposable diaper 1. The longitudinal dimension of die absorbent core 7 extends along the longitudinal axis A from the absorbent core front waist edge 12 to the absorbent core back waist edge 13. The absorbent core 7 also has a transverse dimension extending along the transverse axis B, which is running perpendicular to the longitudinal axis A. The absorbent core 7 has an absorbent core crotch region 16, an absorbent core front waist region 17 which extends from the absorbent core crotch region 16 to the absorbent core front waist edge 12 and makes up 25% of the longitudinal dimension of the absorbent core 7. The absorbent core back waist region 18 extends from the absorbent core crotch region 16 to die absorbent core back waist edge 13 and makes up 25% of the longitudinal dimension of the absorbent core 7. The absorbent core crotch region 16 makes up 50% of the longitudinal dimension of the absorbent core 7.

The configuration and construction of the absorbent core 7 may vary, e.g. the absorbent core 7 may have varying caliper zones, a hydrophilic gradient, a superabsorbent gradient, or lower average density and lower average basis weight acquisition zones. The total absorbent capacity of the absorbent core should, however, be compatible with the design loading and the intended use of the diaper. Further, the size and absorbent capacity of the absorbent core may be varied to accommodate wearers ranging from infants through adults.

In some embodiments, the absorbent material 10 (e.g. the particulate absorbent polymer material) may be distributed unevenly along the longitudinal dimension of the absorbent core 7. For example, the absorbent core crotch region 16 may comprise a higher amount of absorbent material 10 per area compared to the absorbent core front and back waist regions 17 and 18. In some embodiment, the absorbent core hack waist region 18 comprises not more than 0.01 gram of absorbent material per $cm^2$ surface area (i.e. from 0 g of absorbent material per $cm^2$ to 0.01 gram per $cm^2$). In those embodiments, the absorbent core front waist region 17 preferably comprises at least 0.03 gram of absorbent material per $cm^2$, more preferably ate least 0.04 gram per $cm^2$. The absorbent core crotch region 16 preferably comprises at least 0.04 gram of absorbent material per $cm^2$, more preferably at least 0.05 gram per $cm^2$. The amount of absorbent material in the respective region is calculated by determining the weight of absorbent material in this region and is dividing it by the total surface area of the region (hence, the average amount is taken).

In some embodiment, every area of the absorbent core back waist region IS comprises not more than 0.01 gram of absorbent material per $cm^2$. Also, every area of the absorbent core front waist region 17 may comprise at least 0.03 gram of absorbent material per $cm^2$, preferably at least 0.04 grams per $cm^2$, and every area of the absorbent core crotch region 16 may comprise at least 0.04 gram of absorbent material per $cm^2$, preferably at least 0.05 gram per $cm^2$. In a preferred embodiment, the absorbent material 10 comprises at least 90 weight % of particulate absorbent polymer material, more preferably at least 95 weight % and even more preferably 100 weight %.

In some embodiments, such as shown in FIG. 1, file absorbent core back waist edge 13 is longitudinally offset by at least 10% from the chassis back waist edge 19, as it has been found that the absorbent core 7 is not use of in that area of the disposable diaper. The 10% are determined based on the longitudinal extension of the chassis 6. Preferably, the absorbent core back waist edge 13 is longitudinally offset by at least 12% from the chassis back waist edge 19, more preferably by at least 15%. These configurations result in a distribution of the absorbent material only in these regions of the diaper where absorption of liquid is really needed and thus contribute to reduce the bulk of the diaper. The amount of absorbent material may also vary within the absorbent core, e.g. the absorbent core may be profiled in its longitudinal direction to provide most of the absorbent capacity in the front half of the diaper where the liquid discharge occurs predominately. Despite the reduced bulk, it has been found that the removal of the absorbent material in the back waist region of the diaper may be not always easily accepted by some consumers. Surprisingly, the topsheets such as described herein increase the acceptance of the products among consumers as reinforcing the perception of absorbency.

The diaper may further comprise an acquisition system disposed between the topsheet 8 and a wearer facing side of die absorbent core 7, for instance between the cover layer 11 of the absorbent core 7 and the topsheet 8. The acquisition system may be in direct contact with the absorbent core 7. The acquisition system may comprise a single layer or multiple layers, such as an upper acquisition layer 20 facing towards the wearer's skin and a lower acquisition layer 21 facing the garment of the wearer. The acquisition system may function to receive a surge of liquid, such as a gush of urine. In other words, the acquisition system may serve as a temporary reservoir for liquid until the absorbent core can absorb the liquid. The acquisition layer can for example comprise fibrous nonwoven materials made by air laying or wet laying of synthetic fibres such as polyethylene (PE), polyethylene terephthalate (PET), or polypropylene (PP), similarly to the cover layer of the absorbent core. Exemplary materials for the fluid acquisition layer could comprise spunbonded or carded nonwoven materials, or airlaid materials such as for example latex bonded or thermal bonded airlaid materials. Basis weights can typically range from about 10 $g/m^2$ to about 60 $g/m^2$ or from about 25 $g/m^2$ to about 40 $g/m^2$.

In order to keep the disposable diaper 1 in place about the wearer, at least a portion of the chassis back waist region 3 may be attached by the fastening members 22 to at least a portion of the chassis front waist region 2 to form leg opening(s) and an article waist. According to certain embodiments, the disposable diaper 1 may be provided with a re-closable fastening system joined to the chassis for securing the disposable diaper to a wearer, or may alternatively be provided in the form of a pant-type disposable diaper. The fastening system may include at least one fastening member 22 and at least one landing zone 23. In a pant-type disposable diaper, the article may comprise at least two side panels joined to the backsheet 9 and/or topsheet 8 along their longitudinal edges facing towards the longitudinal axis A and joined to each other along their longitudinal edges facing away from the longitudinal axis A to form a pant.

The disposable diaper may have also leg cuffs 24 and/or barrier cuffs. Suitable cuffs are described in for example U.S. Pat. Nos. 3,860,003; 4,808,178 and 4,909; 4,695,278 and 4,795,454. The disposable diaper may also have elastic members 25.

Processes for assembling die diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1.258 or H-2031.

Topsheet Dryness and Rewet

EXAMPLE 1

One layer Spunbonded (S) nonwoven available from Fiberweb Corovin Peine, Germany. The nonwoven is made of polypropylene, has a basis weight of 12 $g/m^2$, and is thermally bonded with round (circular) bonded points, each bonded point having a surface area of 4 mm², the total bonded area being 21% of the total surface area of the material. The bonded points are evenly distributed.

EXAMPLE 2

One layer Spunbonded (S) nonwoven available from Fiberweb Corovin Peine, Germany. The nonwoven is made of polypropylene, has a basis weigh of 15 g/m², and is thermally bonded with round (circular) bonded points, each bonded point having a surface area of 4 mm², the total bonded area being 21% of the total surface area of the material. The bonded points are evenly distributed.

EXAMPLE 3

One layer Spunbonded (S) nonwoven available from Fiberweb Corovin Peine, Germany. The nonwoven is made of polypropylene, has a basis weight of 15 g/m², and is thermally bonded with round (circular) bonded points, each bonded point having a surface area of 4 mm², the total bonded area being 21% of the total surface area of the material. The bonded points are evenly distributed.

EXAMPLE 4

Comparative Example

One layer Spunbonded (S) nonwoven available from Fiberweb Corovin Peine, Germany. The nonwoven is made of polypropylene, has a basis weight of 15 g/m², and is thermally bonded with round (circular) bonded points, each bonded point having a surface area of 4 mm², the total bonded area being 21% of the total surface area of the material. The bonded points are evenly distributed.

Topsheet Dryness Test

The Topsheet Dryness Test determines the amount of liquid retained in the topsheet. This test simulates the in-use performance of diaper. The test should be carried out at about 22±/−2° C. and at 50+/−5% relative humidity.

Sample Preparation and Loading

The test sample comprises an absorbent core including an acquisition system, a topsheet and a backsheet. The absorbent core including the acquisition system of the present sample is as available in diapers sold under the Tradename Pampers® Active Fit, Size 4, sold in the UK. On the topsheet, a rectangular part (55 mm×105 mm) is marked (centered in cross direction) and the leading side of the 55 mm wide rectangular part is placed 28 mm away from the leading edge of the absorbent core.

The synthetic urine used in these test methods is a 0.9% NaCl solution in de-ionized water.

The test sample is arranged to lie flat on a platform of the equipment with the topsheet facing up. Suitable equipment includes equipment as available from FKV S.r.l, Italy. A plate having a 5 cm diameter opening in its middle is placed on top of the sample on the loading zone of the sample. The loading zone is centered under the 5 cm diameter opening. The loading zone of the sample is defined as the zone located at 102 ram from the leading edge of the absorbent core and centered relative to the longitudinal edges of the absorbent core. A pressure of 2.07 kPa is applied to the sample.

The test sample is loaded with a 75 ml gush of synthetic urine at a rate of 15 ml/s using a pump (Model 7520-00, supplied by Cole Parmer Instruments, Chicago, U.S.A.), from a height of 5 cm above the sample surface. The synthetic urine is introduced to the sample through a cylinder fitted in the 5 cm opening of the plate. Precisely 5 minutes after the gush, the sample is loaded again with a 75 ml gush of synthetic urine at a rate of 15 ml/s. The loading step is performed two more times as described herein at precisely 5 minute gush intervals.

Measurement 10 minutes after the absorbance of the 4th gush, the marked topsheet rectangle (55 mm×105 mm) is cut from the sample and put into a petri dish. The weight of the topsheet and petri dish is then measured and recorded as the wet weight.

The marked topsheet rectangular part in the petri dish is placed for 12 hours in a 60° C. preheated oven. The weight of the topsheet and petri dish is then measured and recorded as the dry weight.

The difference between the wet and dry weight is specified as the retained liquid in topsheet.

It was found that topsheets having a basis weight from 12 to 18 gsm were exhibiting an acceptable fluid retention. Nevertheless, topsheets of lower basis weight, from 13 to 16 gsm, were found to perform even better,

|  | Ex 1 12 gsm | Ex 2 15 gsm | Ex 3 18 gsm | Ex 4 25 gsm |
| --- | --- | --- | --- | --- |
| Liquid in topsheet [mg] | 74.0 | 121.9 | 155.6 | 419.0 |

Rewet Test

The rewet test determines the is use performance of a diaper. It measures the amount of liquid which is released by the topsheet. High rewet properties are not desirable since they would make the wearers uncomfortable. The test should be carried out at about 22+/−2° C. and at 50+/−5% relative humidity.

Sample Preparation and Loading

The sample is prepared and loaded as described above.

Measurement

Before executing the test, a collagen film as purchased from NATURIN GmbH, Weinhein, Germany, under die designation of COFFI and at a basis weight of about 28 g/m² is prepared by being cut into sheets of 70 mm diameter e.g. by using a sample cutter device, and by equilibrating the film in the controlled environment of the test room (see above) for at least 12 hours (tweezers are to be used for all handling of the collagen film).

10 minutes after die last gush of the sample load preparation is absorbed, the test sample is carefully placed flat on a lab bench.

4 sheets of the precut and equilibrated collagen material are weighed with at least one milligram accuracy, and then positioned centered onto the loading point of the topsheet (i.e. point centered relative to the longitudinal edges of the absorbent core and 102 mm away from the leading edge of the absorbent core) and covered by perspex plate of 90 mm diameter, and about 20 mm thickness. A weight of 9.1 kg is carefully added (also centered). After 30+/−2 seconds the weight and perspex plate are carefully removed again, and the collagen films are reweighed.

The difference between the weight of the dry collagen sheets and the wet collagen sheets after load is the moisture pick up of die collagen film, expressed in mg.

It was found that topsheets having a basis weight from 12 to 18 gsm were exhibiting an acceptable rewet. Nevertheless, topsheets of lower basis weight, from 13 to 16 gsm, were found to perform even better.

|  | Ex 1<br>12 gsm | Ex 2<br>15 gsm | Ex 3<br>18 gsm | Ex 4<br>25 gsm |
|---|---|---|---|---|
| Rewet all 9.1 kg/10 min [g] | 0.041 | 0.041 | 0.052 | 0.072 |

Every document cited herein, including any cross referenced or related patent or application, is hereby incorporated herein by reference in its entirety unless expressly excluded or otherwise limited. The citation of any document is not an admission that it is prior art with, respect to any invention disclosed or claimed herein or that it alone, or in any combination with any other reference or references, teaches, suggests or discloses any such invention. Further, to the extent that any meaning or definition of a term it) this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both, the recited value and a functionally equivalent range surrounding that value. For example, a dimension disclosed as "40 mm" is intended to mean "about 40 mm."

What is claimed is:

1. A disposable diaper comprising a colored topsheet, wherein said topsheet has a basis weight of from about 12 gsm to about 18 gsm and comprises a plurality of bonded points, wherein each of said points has a surface area of from 2 mm$^2$ to 5 mm$^2$ and wherein the cumulated surface area of the plurality of bonded points is from 10% to 25% of the total surface area of the topsheet.

2. The disposable diaper according to claim 1 wherein said topsheet comprises at least about 20% of thermoplastic fibers.

3. The disposable diaper according to claim 1 wherein said topsheet has a basis weight of from about 13 gsm to about 16 gsm.

4. The disposable diaper according to claim 1 wherein each of said bonded points has a surface area of from about 2.5 mm$^2$ to about 4.5 mm$^2$ and/or wherein the cumulated surface area of said points is from about 14% to about 22% of the total surface area of the topsheet.

5. The disposable diaper according to claim 1 wherein the color of the topsheet is selected from the group consisting of pink, red, blue, green, orange, yellow, periwinkle and any declination or mixture thereof.

6. The disposable diaper according to claim 1 wherein each of said bonding points has a shape which is selected from the group consisting of circular, diamond, oval, rectangular, triangular and square.

7. The disposable diaper according to claim 1 wherein said bonded points are thermally bonded points.

8. The disposable diaper according to claim 1, wherein said diaper comprises:
   a chassis, said chassis having a longitudinal dimension, a chassis back waist edge and a chassis front waist edge;
   an absorbent core disposed in said chassis, said absorbent core having a longitudinal dimension co-extending with the longitudinal dimension of said chassis, an absorbent core back waist edge and absorbent core front waist edge;
   wherein said absorbent core back waist edge is longitudinally offset by at least 10% from said chassis back waist edge, the 10% offset being based on the longitudinal dimension of said chassis.

9. The disposable diaper according to claim 8 wherein the absorbent core comprises one or more absorbent structure, wherein each of said absorbent structure comprises a nonwoven substrate layer supporting particulate absorbent polymer material, said particulate absorbent polymer material being immobilized on the nonwoven substrate layer by a thermoplastic adhesive composition, which forms a fibrous network over the particulate absorbent polymer material.

10. The disposable diaper according to claim 1 wherein said topsheet is made of a nonwoven material comprising fibers selected from the group consisting of synthetic fibers and combinations of synthetic fibers and natural fibers.

11. The disposable diaper according to claim 1 wherein said topsheet is a dual layer spunbond.

12. The disposable diaper according to claim 1 wherein said topsheet is a tri-layer spunbond.

13. The disposable diaper according to claim 1 wherein said topsheet is made of polypropylene fibers.

14. The disposable diaper according to claim 1 wherein the plurality of bonded points is evenly distributed over the surface of the topsheet.

15. The disposable diaper according to claim 1 wherein said topsheet is coextensive with a chassis of said diaper.

* * * * *